United States Patent
Bubendorf et al.

(10) Patent No.: US 7,148,231 B2
(45) Date of Patent: Dec. 12, 2006

(54) [6,7-BIS(2-METHOXY-ETHOXY)-QUINAZOLIN-4-YL]-(3-ETHYNYL-PHENYL)AMINE HYDROCHLORIDE POLYMORPH

(75) Inventors: Andre Gerard Bubendorf, Uffheim (FR); Michael Hennig, Weil am Rhein (DE); Pirmin Hidber, Basel (CH); Goesta Rimmler, Bad Krozingen (DE); Franziska Rohrer, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 24 days.

(21) Appl. No.: 10/771,217

(22) Filed: Feb. 3, 2004

(65) Prior Publication Data

US 2004/0162300 A1     Aug. 19, 2004

(30) Foreign Application Priority Data

Feb. 17, 2003     (EP)     .................................. 03003587

(51) Int. Cl.
*A61K 31/505* (2006.01)
*C07D 239/04* (2006.01)

(52) U.S. Cl. ..................... 514/266.4; 544/293

(58) Field of Classification Search ............. 514/266.3, 514/266.4; 544/293
See application file for complete search history.

(56) References Cited

FOREIGN PATENT DOCUMENTS

| EP | 1 044 969 A2 | 10/2000 |
|---|---|---|
| WO | WO 96/30347 | 10/1996 |
| WO | WO 99/55683 A1 | 11/1999 |
| WO | WO 01/34574 | 5/2001 |

*Primary Examiner*—James O. Wilson
*Assistant Examiner*—Tamthom N. Truong
(74) *Attorney, Agent, or Firm*—George W. Johnston; Patricia S. Rocha-Tramaloni; David E. Wildman

(57) ABSTRACT

The invention is concerned with a novel polymorph of [6,7-Bis(2-methoxy-ethoxy)-quinazolin-4-yl]-(3-ethynyl-phenyl)amine hydrochloride. This polymorph exhibits superior properties compared to the previously known forms of [6,7-Bis(2-methoxy-ethoxy)-quinazolin-4-yl]-(3-ethynyl-phenyl)amine hydrochloride. The [6,7-Bis(2-methoxy-ethoxy)-quinazolin-4-yl]-(3-ethynyl-phenyl)amine hydrochloride is an inhibitor of tyrosine kinase enzymes, and are useful in the treatment of cancer. Also disclosed are methods of making and using the novel polymorph, as well as pharmaceutical compositions containing the novel polymorph.

7 Claims, 6 Drawing Sheets

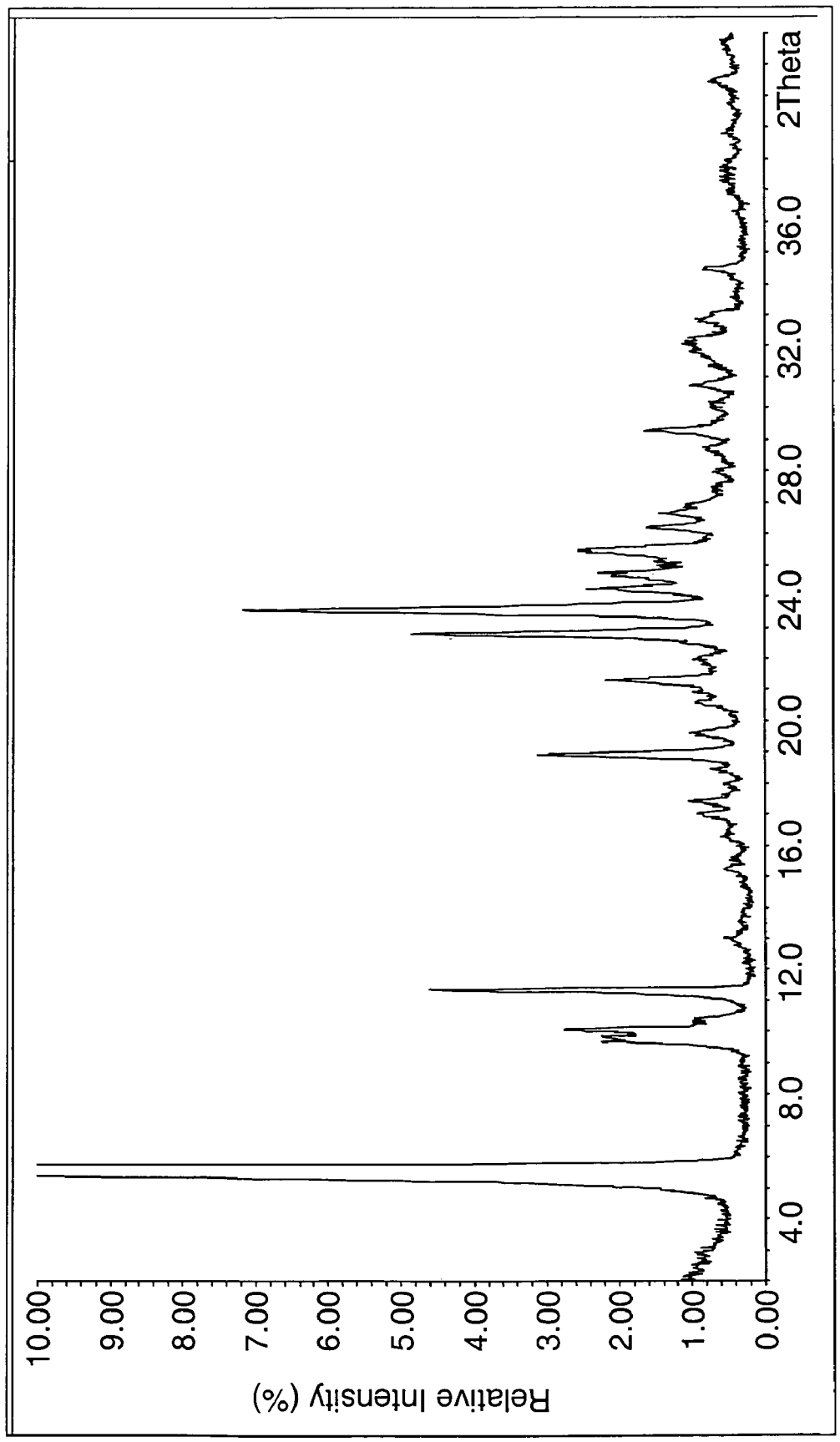
Figure 1: X-ray diffraction pattern of polymorph E

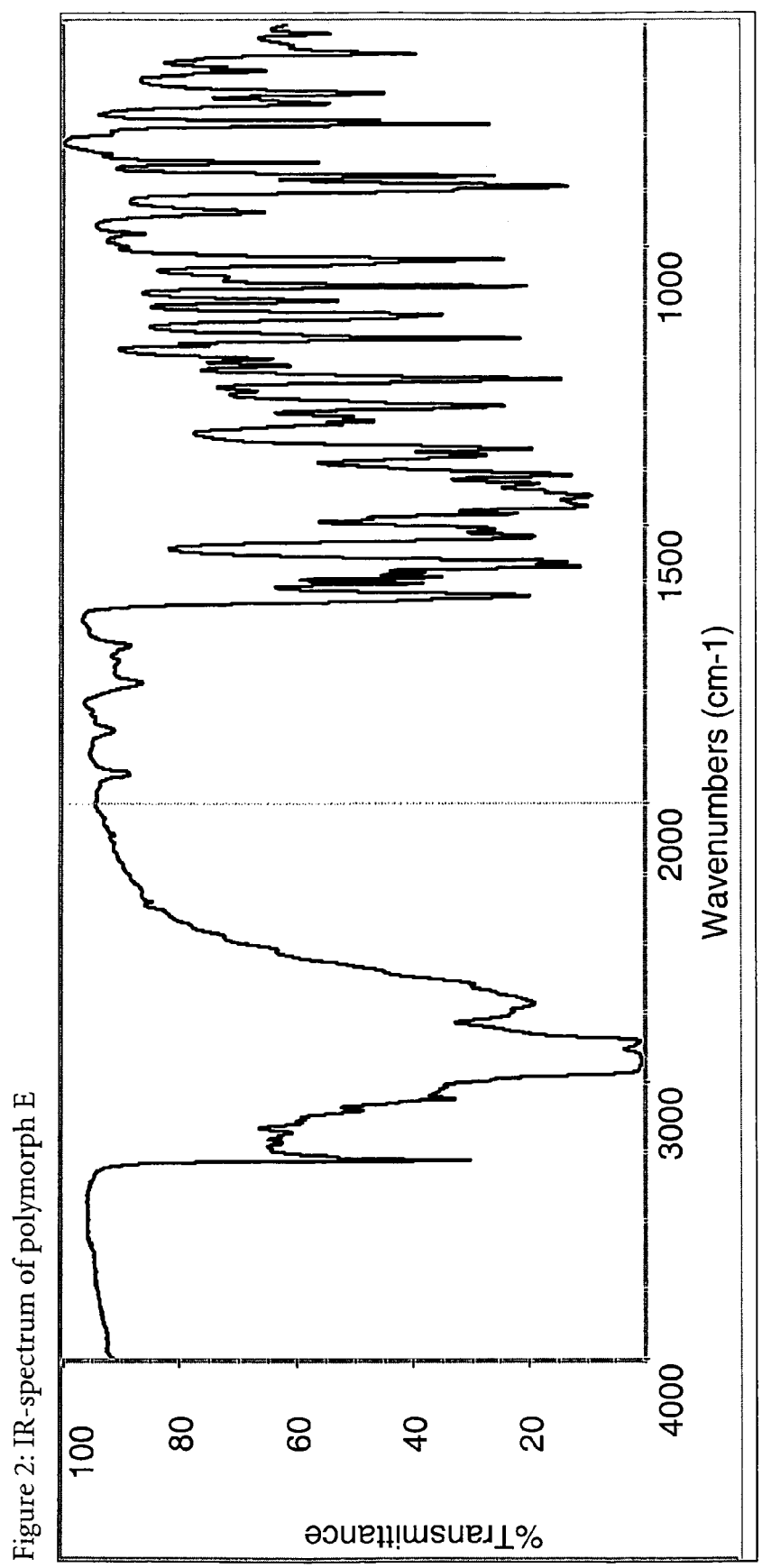

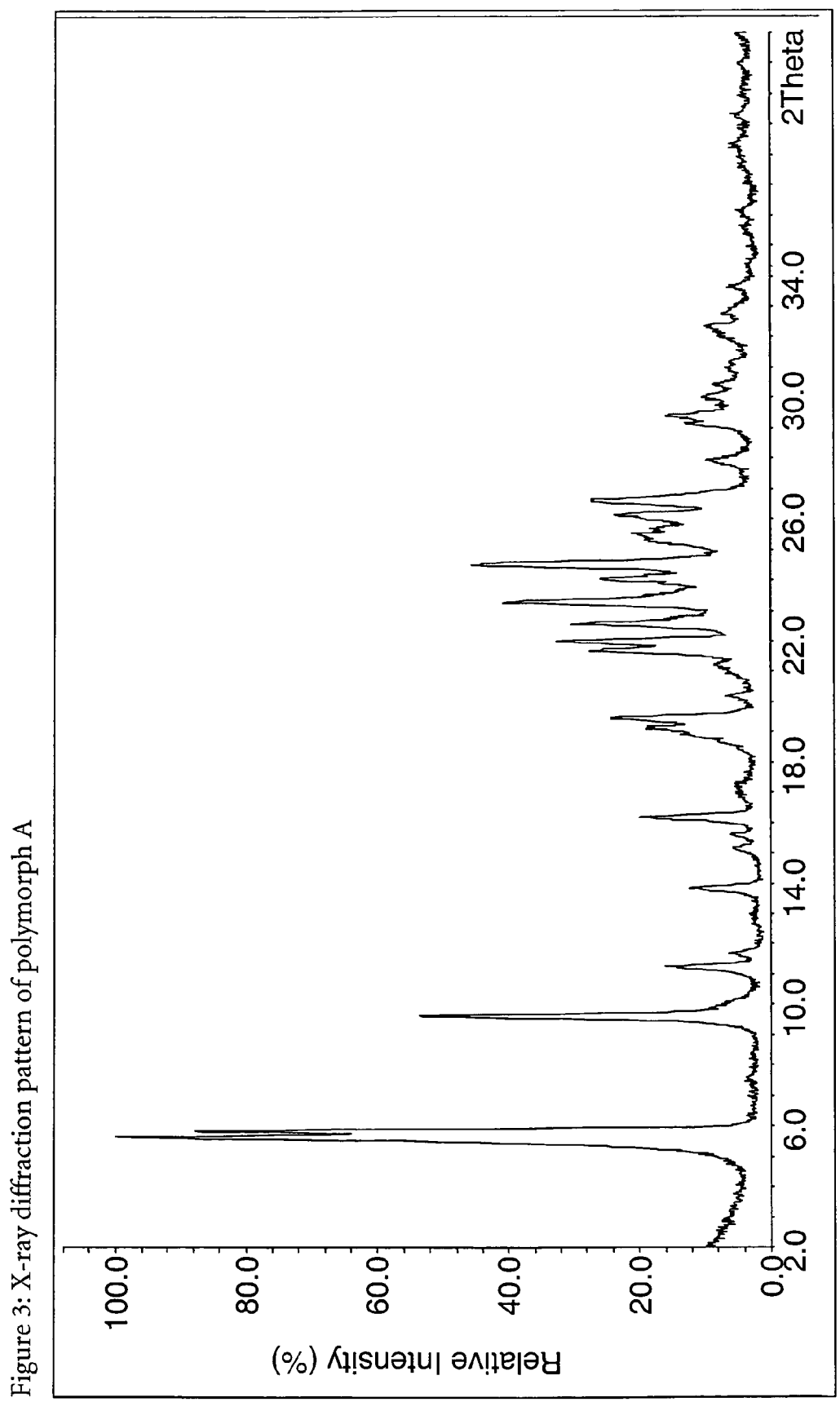
Figure 3: X-ray diffraction pattern of polymorph A

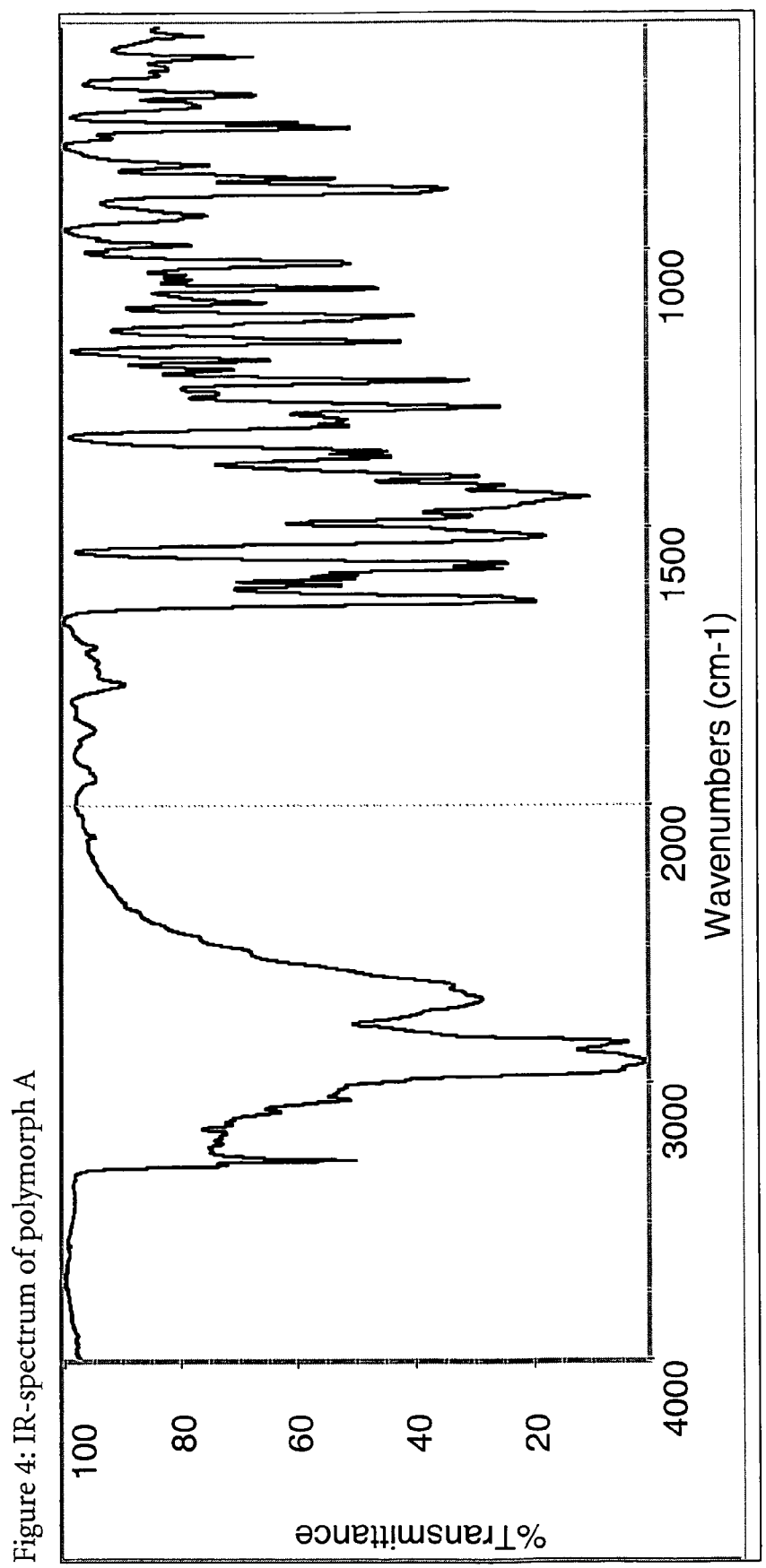
Figure 4: IR-spectrum of polymorph A

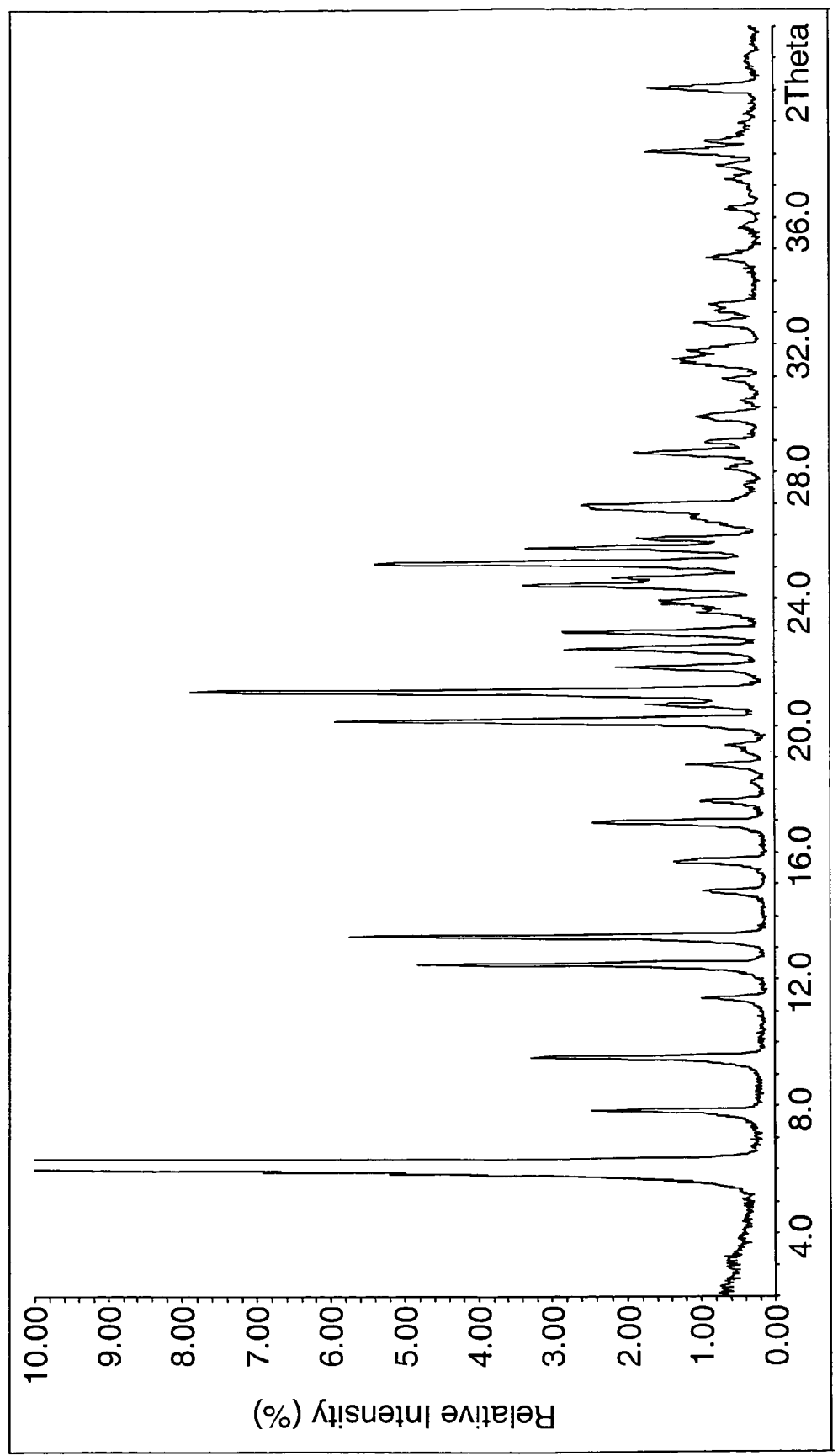
Figure 5: X-ray diffraction pattern of polymorph B

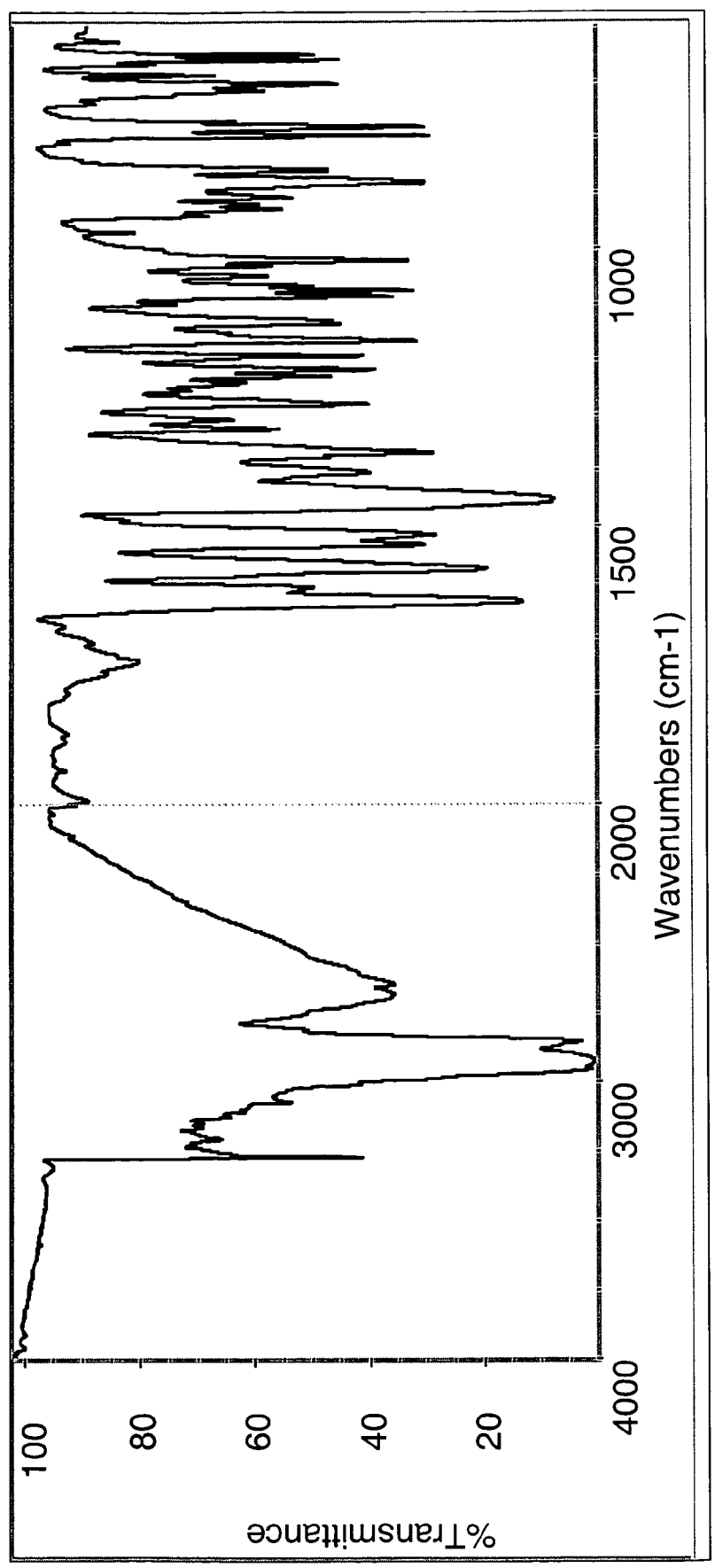

[6,7-BIS(2-METHOXY-ETHOXY)-QUINAZOLIN-4-YL]-(3-ETHYNYL-PHENYL)AMINE HYDROCHLORIDE POLYMORPH

FIELD OF THE INVENTION

The present invention relates to a crystalline polymorph of [6,7-Bis(2-methoxy-ethoxy)-quinazolin-4-yl]-(3-ethynyl-phenyl)amine hydrochloride, processes for its manufacture, pharmaceutical compositions containing the polymorphs, and the use of the polymorph in the treatment of hyperproliferative disorders, such as cancer, in mammals.

BACKGROUND OF THE INVENTION

In WO 96/30347, the preparation of [6,7-Bis(2-methoxy-ethoxy)-quinazolin-4-yl]-(3-ethynyl-phenyl)amine hydrochloride as well as the uses of this compound have been disclosed. This compound is depicted in formula (I).

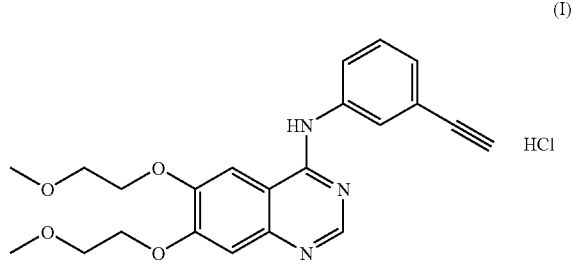

(I)

In particular, this compound is an inhibitor of tyrosine kinase enzymes such as epidermal growth factor receptors and can be used for the treatment and/or prevention of diseases which are associated with tyrosine kinase enzymes such as epidermal growth factor receptors, such as cancer, particularly non small cell lung cancer, colorectal cancer, refractory non small cell lung cancer, pancreatic cancer, ovarian cancer, breast cancer, glioma, head cancer or neck cancer.

Recently, two different polymorphs of [6,7-bis(2-methoxy-ethoxy)-quinazolin-4-yl]-(3-ethynyl-phenyl)amine hydrochloride, designated as polymorph A and polymorph B, have been disclosed in WO 01/34574.

Polymorphism is defined as the ability of a substance to crystallize in more than one crystal lattice arrangement. Polymorphism can influence many aspects of solid state properties of a drug. Different crystal modifications of a substance may differ considerably from one another in many respects such as their solubility, dissolution rate and finally bioavailability. An exhaustive treatment of polymorphism in pharmaceutical and molecular crystals is given e.g., by Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

Of the two polymorphs described in WO 01/34574, polymorph B is thermodynamically more stable than polymorph A, while polymorph A exhibits a better solubility and dissolution rate than polymorph B. However, based on the known polymorphs A and B of [6,7-Bis(2-methoxy-ethoxy)-quinazolin-4-yl]-(3-ethynyl-phenyl)amine hydrochloride, it was still considered desirable to have a form of this compound which, while being thermodynamically more stable than polymorph A, also exhibits a better solubility and dissolution rate than polymorph B.

SUMMARY OF THE INVENTION

Surprisingly, it has now been found that [6,7-Bis(2-methoxy-ethoxy)-quinazolin-4-yl]-(3-ethynyl-phenyl)amine hydrochloride can exist in a third polymorphic form, designated as polymorph E, which is thermodynamically more stable than the known polymorph A and exhibits a better solubility and dissolution rate than the known polymorph B.

Thus, in one embodiment, the present invention relates to a novel crystalline polymorph of [6,7-Bis(2-methoxy-ethoxy)-quinazolin-4-yl]-(3-ethynyl-phenyl)amine hydrochloride which unexpectedly exhibits the desired increased solubility and dissolution rate with respect to polymorph B and an increased thermodynamic stability compared to polymorph A. The polymorph of the present invention will consequently have improved pharmacological properties when compared to the known polymorphs A and B.

In another embodiment, the invention relates to a method of making the above-mentioned polymorph E.

In another embodiment, the invention relates to pharmaceutical compositions containing a therapeutically effective amount of polymorph E and a pharmaceutically acceptable carrier or excipient.

DETAILED DESCRIPTION OF THE INVENTION

Unless otherwise indicated, the following definitions are set forth to illustrate and define the meaning and scope of the various terms used to describe the invention herein.

The term "crystalline polymorph" refers to a crystal modification which can be characterized by analytical methods such as e.g., X-ray powder diffraction, IR-spectroscopy or by its melting point.

The term "polymorph E" relates to the crystalline polymorph of [6,7-Bis(2-methoxy-ethoxy)-quinazolin-4-yl]-(3-ethynyl-phenyl)amine hydrochloride of the present invention. The terms "polymorph A" and "polymorph B" relate to different crystalline polymorphs of [6,7-Bis(2-methoxy-ethoxy)-quinazolin-4-yl]-(3-ethynyl-phenyl)amine hydrochloride as described in WO 01/34574.

The term "IR" means infrared.

DESCRIPTION OF FIGURES

FIG. 1: X-ray diffraction pattern of polymorph E
FIG. 2: IR-spectrum of polymorph E
FIG. 3: X-ray diffraction pattern of polymorph A
FIG. 4: IR-spectrum of polymorph A
FIG. 5: X-ray diffraction pattern of polymorph B
FIG. 6: IR-spectrum of polymorph B In detail, the present invention relates to a crystalline polymorph of [6,7-Bis(2-methoxy-ethoxy)-quinazolin-4-yl]-(3-ethynyl-phenyl)amine hydrochloride which is characterized by an X-ray powder diffraction pattern having characteristic peaks expressed in degrees 2-theta at approximately

| degree 2-theta |
| --- |
| 5.7 |
| 9.7 |
| 10.1 |
| 11.3 |
| 17.0 |
| 17.4 |
| 18.9 |
| 19.6 |
| 21.3 |
| 22.8 |
| 23.6 |
| 24.2 |
| 24.7 |
| 25.4 |
| 26.2 |
| 26.7 |
| 29.3 |

The X-ray powder diffraction patterns of the individual crystalline polymorphs herein were recorded with a Bruker D8 diffractometer (geometry: Bragg-Brentano; radiation: CuKα 1.54184 Å; graphite secondary monochromator; detector: scintillation counter, 2δ step scan with a step size of 0.02° and a measuring time of 1.0 s per step). The samples (approximately 200 mg) were prepared and analyzed without further processing (e.g., grinding or sieving) of the substance.

The term "approximately" means in this context that there is an uncertainty in the measurements of the degrees 2-theta of ±0.2 (expressed in degrees 2-theta).

Preferably, the crystalline polymorph as described above is characterized by the X-ray powder diffraction pattern having characteristic peaks expressed in degrees 2-theta as described above, which have relative intensities of approximately

| degree 2-theta | relative intensity |
| --- | --- |
| 5.7 | 100 |
| 9.7 | 2.7 |
| 10.1 | 3.3 |
| 11.3 | 4.4 |
| 17.0 | 1.2 |
| 17.4 | 1.4 |
| 18.9 | 3.9 |
| 19.6 | 1.2 |
| 21.3 | 2.6 |
| 22.8 | 5.1 |
| 23.6 | 9.0 |
| 24.2 | 3 |
| 24.7 | 2.7 |
| 25.4 | 3.2 |
| 26.2 | 2.2 |
| 26.7 | 1.8 |
| 29.3 | 2 |

The term "approximately" means in this context that there is an uncertainty in the measurements of the relative intensities. It is known to the person skilled in the art that the uncertainty of the relative intensities depends strongly on the measurement conditions. The relative intensity values can e.g., vary by ±30% or preferably by ±10%.

Preferred is a crystalline polymorph as described above, which is characterized by the x-ray powder diffraction pattern shown in FIG. 1.

The crystalline polymorph described above can be characterized by its IR spectrum. In a further preferred embodiment, the invention relates to a crystalline polymorph of [6,7-Bis(2-methoxy-ethoxy)-quinazolin-4-yl]-(3-ethynyl-phenyl)amine hydrochloride which is characterized by an IR absorption spectrum having characteristic peaks expressed in cm$^{-1}$ at approximately 3277 cm$^{-1}$, 3057 cm$^{-1}$, 1627 cm$^{-1}$,1070 cm$^{-1}$, 1022 cm$^{-1}$, 892 cm$^{-1}$, 873 cm$^{-1}$, 850 cm$^{-1}$, 780 cm$^{-1}$, 745 cm$^{-1}$725 cm$^{-1}$652 cm$^{-1}$. The term "approximately" means in this context that the cm$^{-1}$ values can vary by ±2 cm$^{-1}$, preferably by ±1 cm$^{-1}$. The crystalline polymorph as described above, characterized by the IR absorption spectrum shown in FIG. 2, is an embodiment of the present invention.

In addition, the crystalline polymorph described above can be characterized by its melting point. Therefore, the invention also embraces a crystalline polymorph of [6,7-Bis (2-methoxy-ethoxy)-quinazolin-4-yl]-(3-ethynyl-phenyl) amine hydrochloride which is characterized by a melting point of 211° C. to 214° C.

Moreover, the invention relates especially to the compound [6,7-Bis(2-methoxy-ethoxy)-quinazolin-4-yl]-(3-ethynyl-phenyl)amine hydrochloride, wherein at least 70% are a crystalline polymorph as defined above, particularly wherein at least 90% are a crystalline polymorph as defined above, more particularly wherein at least 95% are a crystalline polymorph as defined above and even more particularly wherein at least 99% are a crystalline polymorph as defined above.

The invention further relates to a process for the manufacture of a crystalline polymorph as described above, which process comprises reacting a compound of formula (II)

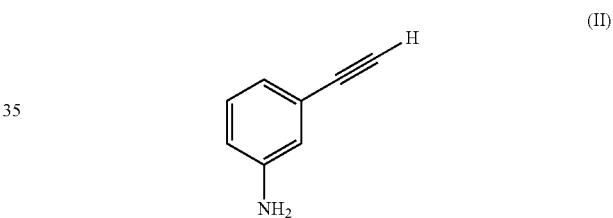

(II)

with a compound of formula (III)

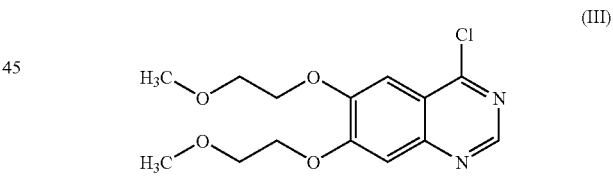

(III)

in (α,α,α)-trifluorotoluene. The compound of formula (II) is 3-ethynylaniline, also referred to as 3-ethynyl-aminobenzene, and the compound of formula (III) is 4-chloro-6,7-bis (2-methoxyethoxy)quinazoline. The starting products of formula (II) and (III) can be obtained according to methods known in the art, e.g., from WO 01/34574. The reaction described above can be carried out under conditions known to a person skilled in the art. For example, an appropriate temperature would be 30 to 100° C., preferably 50 to 80° C., more preferably 70 to 80° C. In a preferred embodiment, the reaction is carried out in the presence of HCl. When the reaction is performed, the crystalline polymorph of [6,7-Bis (2-methoxy-ethoxy)-quinazolin-4-yl]-(3-ethynyl-phenyl) amine hydrochloride as described above, precipitates from the (α,α,α)-trifluorotoluene and can be isolated by methods known to the person skilled in the art, e.g., by filtration or centrifugation. The molar ratio of compound of formula (II) to compound of formula (III) can be varied, e.g., in the range of 0.5 to 1.5. Preferably, the molar ratio is in the range of 0.9 to 1.1. More preferably, the molar ratio is about 1, most preferably 1.

Furthermore, the invention relates to a crystalline polymorph as defined above, when manufactured by a process as described above.

As described above, the polymorph of the present invention is a pharmaceutically active compound and inhibits tyrosine kinase enzymes, particularly epidermal growth factor receptors. This polymorph can be used for the treatment and/or prevention of diseases which are associated with tyrosine kinase enzymes, particularly epidermal growth factor receptors, such as cancer, particularly non small cell lung cancer, colorectal cancer, refractory non small cell lung cancer, pancreatic cancer, ovarian cancer, breast cancer, glioma, head cancer or neck cancer. Prevention and/or treatment of non small cell lung cancer is the preferred indication.

The invention therefore also relates to pharmaceutical compositions comprising a crystalline polymorph as defined above and a pharmaceutically acceptable carrier and/or adjuvant.

The invention likewise embraces a crystalline polymorph as described above for use as therapeutically active substances, especially as therapeutically active substances for the treatment and/or prophylaxis of diseases which are associated with tyrosine kinase enzymes, particularly epidermal growth factor receptors, particularly as therapeutically active substances for the treatment and/or prophylaxis of cancer, particularly non small cell lung cancer, colorectal cancer, refractory non small cell lung cancer, pancreatic cancer, ovarian cancer, breast cancer, glioma, head cancer or neck cancer, more particularly non small cell lung cancer.

In another preferred embodiment, the invention relates to a method for the therapeutic and/or prophylactic treatment of diseases which are associated with tyrosine kinase enzymes, particularly epidermal growth factor receptors, particularly for the therapeutic and/or prophylactic treatment of cancer, particularly non small cell lung cancer, colorectal cancer, refractory non small cell lung cancer, pancreatic cancer, ovarian cancer, breast cancer, glioma, head cancer or neck cancer, more particularly non small cell lung cancer, which method comprises administering a crystalline polymorph as defined above to a human being or animal.

The invention also embraces the use of a crystalline polymorph as defined above for the therapeutic and/or prophylactic treatment of diseases which are associated with tyrosine kinase enzymes, particularly epidermal growth factor receptors, particularly for the therapeutic and/or prophylactic treatment of cancer, particularly non small cell lung cancer, colorectal cancer, refractory non small cell lung cancer, pancreatic cancer, ovarian cancer, breast cancer, glioma, head cancer or neck cancer, more particularly non small cell lung cancer.

The invention also relates to the use of a crystalline polymorph as described above for the preparation of medicaments for the therapeutic and/or prophylactic treatment of diseases which are associated with tyrosine kinase enzymes, particularly epidermal growth factor receptors, particularly for the therapeutic and/or prophylactic treatment of cancer, particularly non small cell lung cancer, colorectal cancer, refractory non small cell lung cancer, pancreatic cancer, ovarian cancer, breast cancer, glioma, heac cancer, neck cancer, more particularly non small cell lung cancer. Such medicaments comprise a compound as described above.

In the compositions, uses and methods as described above, the compound [6,7-Bis (2-methoxy-ethoxy)-quinazolin-4-yl]-(3-ethynyl-phenyl)amine hydrochloride, wherein at least 70% are a crystalline polymorph as defined above, particularly wherein at least 90% are a crystalline polymorph as defined above, more particularly wherein at least 95% are a crystalline polymorph as defined above and even more particularly wherein at least 99% are a crystalline polymorph as defined above, can be used instead of the polymorph as defined above.

The polymorph of the present invention can be used as medicament, e.g., in the form of pharmaceutical preparations for enteral, parenteral or topical administration. It can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils.

The production of the pharmaceutical preparations can be effected in a manner which will be familiar to any person skilled in the art by bringing the described polymorph, optionally in combination with other therapeutically valuable substances, into a galenical administration form together with suitable, non-toxic, inert, therapeutically compatible solid or liquid carrier materials and, if desired, usual pharmaceutical adjuvants. As used herein, the term "adjuvant" refers to carriers and/or excipients.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants are possible pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 7000 mg, especially about 5 to 2500 mg, preferably 5 to 200 mg comes into consideration. Depending on severity of the disease and the precise pharmacokinetic profile the compound could be administered with one or several daily dosage units, e.g., in 1 to 3 dosage units.

The pharmaceutical preparations conveniently contain about 1–1000 mg, preferably 5–200 mg of a compound of formula I.

The following examples illustrate the present invention in more detail. They are, however, not intended to limit its scope in any manner. The crystalline polymorphs A and B of [6,7-Bis(2-methoxy-ethoxy)-quinazolin-4-yl]-(3-ethynyl-phenyl)amine hydrochloride can be obtained according to the methods disclosed in WO 01/34574.

EXAMPLES

Example 1

A 500 mL jacketed reactor is purged at room temperature with nitrogen and charged with 30 g of 4-chloro-6,7-bis(2-methoxyethoxy)quinazoline and 130 g of (α,α,α)-trifluorotoluene. To the white suspension 12.55 g 3-ethynylaniline dissolved in 180 g (α,α,α)-trifluorotoluene are added. After adding 0.18 g HCl (37%), the reaction mixture is stirred for another 15 min at room temperature and then heated to reflux temperature. After completion of the reaction, the suspension is cooled to room temperature and filtered. The isolated crystals of [6,7-Bis(2-methoxy-ethoxy)-quinazolin-4-yl]-(3-ethynyl-phenyl)amine hydrochloride are washed with ethanol and dried at 60° C./10 mbar overnight. The dry final product is characterized by means of X-ray powder diffraction and IR-spectroscopy as modification E. The crystals melt around 213° C. ($T_{onset}$, measured by differential scanning calorimetry).

Example 2

The X-ray powder diffraction patterns of the individual crystalline polymorphs E, A and B of [6,7-Bis(2-methoxy-ethoxy)-quinazolin-4-yl]-(3-ethynyl-phenyl)amine hydrochloride were recorded with a Bruker D8 diffractometer (geometry: Bragg-Brentano; radiation: CuKα 1.54184 Å; graphite secondary monochromator; detector: scintillation counter, 2δ step scan with a step size of 0.02° and a measuring time of 1.0 s per step). The samples (approximately 200 mg) were prepared and analyzed without further processing (e.g., grinding or sieving) of the substance. The X-ray powder diffraction patterns of the individual crystalline polymorphs E, A and B of [6,7-Bis (2-methoxy-ethoxy)-quinazolin-4-yl]-(3-ethynyl-phenyl)amine hydrochloride are shown in FIGS. 1, 3 and 5 respectively.

Example 3

The IR-spectra of the individual crystalline polymorphs E, A and B of [6,7-Bis (2-methoxy-ethoxy)-quinazolin-4-yl]-(3-ethynyl-phenyl)amine hydrochloride were recorded as film of a suspension in Nujol consisting of approximately 15 mg of sample and approximately 15 mg of Nujol between two sodium chloride plates, with a FT-IR spectrometer (Nicolet 20SXB or equivalent) in transmittance mode (resolution 2 cm$^{-1}$, 200 or more coadded scans, MCT detector). The IR-spectra of the individual crystalline polymorphs E, A and B of [6,7-Bis(2-methoxy-ethoxy)-quinazolin-4-yl]-(3-ethynyl-phenyl)amine hydrochloride are shown in FIGS. 2, 4 and 6 respectively.

Example 4

The melting points of the individual crystalline polymorphs E, A and B of [6,7-Bis (2-methoxy-ethoxy)-quinazolin-4-yl]-(3-ethynyl-phenyl)amine hydrochloride were obtained by differential scanning calorimetry as described e.g., by P. J. Haines, ed., "Principles of Thermal Analysis and Calorimetry", Royal Society of Chemistry, Cambridge, UK, 2002):

|  | Melting point ($T_{onset}$)/[° C.] |
| --- | --- |
| polymorph E | 211 to 214 |
| polymorph A | 205 to 208 |
| polymorph B | 227 to 231 |

Example 5

The thermodynamic stability of the individual crystalline polymorphs E, A and B of [6,7-Bis(2-methoxy-ethoxy)-quinazolin-4-yl]-(3-ethynyl-phenyl)amine hydrochloride were measured according to methods known in the art, e.g., from Byrn (Byrn, S. R., Pfeiffer, R. R., Stowell, J. G., "Solid-State Chemistry of Drugs", SSCI Inc., West Lafayette, Ind., 1999). Measurements of melting point, heat of solution, as well as equilibration experiments in suspension show that polymorph E is thermodynamically more stable than polymorph A and that polymorph B is more stable than polymorphs E and A.

|  | melting point ($T_{onset}$) [° C.] | heat of solution ethanol/water (45:55 g/g, 45° C.) [kJ/mol] |
| --- | --- | --- |
| polymorph E | 211 to 214 | 56.9 to 58.4 |
| polymorph A | 205 to 208 | 50.0 to 55.6 |
| polymorph B | 227 to 231 | 61.2 to 62.4 |

Example 6

The solubility of polymorphs A, B, and E measured after 20 min equilibration at 20° C. in either water or aqueous buffer solution (pH 1) are compiled the following table.:

|  | water | aqueous buffer (pH 1) |
| --- | --- | --- |
| polymorph E | 0.191% | 0.011% |
| polymorph A | 0.194% | 0.017% |
| polymorph B | 0.098% | 0.003% |

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

-continued

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavoring additives and filled into sachets.

The invention claimed is:

1. A crystalline polymorph of [6,7-Bis(2-methoxy-ethoxy)-quinazolin-4-yl]-(3-ethynyl-phenyl)amine hydrochloride which has a melting point onset temperature of 211° C. to 214° C. and which has an X-ray powder diffraction pattern having characteristic peaks expressed in degrees 2-theta at approximately

| degree 2-theta |
|---|
| 5.7 |
| 9.7 |
| 10.1 |
| 11.3 |
| 17.0 |
| 17.4 |
| 18.9 |
| 19.6 |
| 21.3 |
| 22.8 |
| 23.6 |
| 24.2 |
| 24.7 |
| 25.4 |
| 26.2 |
| 26.7 |
| 29.3. |

2. The crystalline polymorph of claim 1, which has the x-ray powder diffraction pattern shown in FIG. 1.

3. The crystalline polymorph of claim 1 which has an IR absorption spectrum having characteristic peaks expressed in $cm^{-1}$ approximately 3277 $cm^{-1}$, 3057 $cm^{-1}$, 1627 $cm^{-1}$, 1070 $cm^{-1}$, 892 $cm^{-1}$, 873 $cm^{-1}$, 850 $cm^{-1}$, 780 $cm^{-1}$, 745 $cm^{-1}$, 725 $cm^{-1}$, and 652 $cm^{-1}$.

4. The compound [6,7-Bis(2-methoxy-ethoxy)-quinazolin-4-yl]-(3-ethynyl-phenyl)amine hydrochloride, at least 70% of which is present as the crystalline polymorph of claim 1.

5. A process for the manufacture of the crystalline polymorph as defined in claim 1, which process comprises reacting a compound of formula (II)

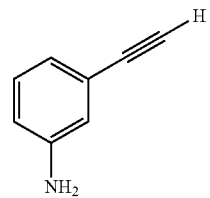

(II)

with a compound of formula (III)

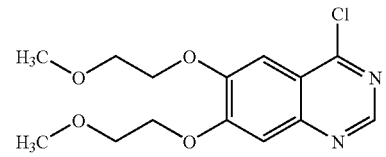

(III)

in $(\alpha,\alpha,\alpha)$-trifluorotoluene.

6. A pharmaceutical composition comprising the crystalline polymorph according to claim 1 and a pharmaceutically acceptable excipient.

7. A method of treating non small cell lung cancer, colorectal cancer, refractory small cell lung cancer, pancreatic cancer, ovarian cancer, breast cancer, glioma, head cancer or neck cancer comprising administering to a patient in need of such treatment a therapeutically effective amount of the crystalline polymorph of claim 1.

* * * * *